(12) United States Patent
Gibbs

(10) Patent No.: US 7,502,111 B2
(45) Date of Patent: Mar. 10, 2009

(54) DIFFERENTIAL OPTICAL TECHNIQUE FOR CHIRAL ANALYSIS

(75) Inventor: Phillip R. Gibbs, Atlanta, GA (US)

(73) Assignee: Stheno Corporation, Atlanta, GA (US)

( * ) Notice: Subject to any disclaimer, the term of this patent is extended or adjusted under 35 U.S.C. 154(b) by 304 days.

(21) Appl. No.: 10/995,118

(22) Filed: Nov. 24, 2004

(65) Prior Publication Data

US 2005/0128482 A1 Jun. 16, 2005

(51) Int. Cl.
*G01J 4/00* (2006.01)

(52) U.S. Cl. ...................................... 356/364
(58) Field of Classification Search ............... None
See application file for complete search history.

(56) References Cited

U.S. PATENT DOCUMENTS

| | | | |
|---|---|---|---|
| 3,740,151 | A | 6/1973 | Chaney et al. |
| 4,011,451 | A | 3/1977 | Nelson |
| 4,276,475 | A | 6/1981 | Nelson |
| 4,498,774 | A | 2/1985 | Yeung et al. |
| 5,168,326 | A | 12/1992 | Tokieda et al. |
| 5,209,231 | A | 5/1993 | Cote et al. |
| 5,276,376 | A | 1/1994 | Puskas |
| 5,286,941 | A | 2/1994 | Bel |
| 5,477,327 | A | 12/1995 | Bergman |
| 5,621,528 | A | 4/1997 | Rokos |
| 5,822,067 | A | 10/1998 | Yanik |
| 5,896,198 | A | 4/1999 | Chou et al. |
| 5,909,642 | A | 6/1999 | Suzuki |
| 6,166,807 | A | 12/2000 | Tatsurou et al. |
| 6,310,522 | B1 | 10/2001 | Wang et al. |
| 6,327,037 | B1 | 12/2001 | Chou et al. |
| 6,466,320 | B1 | 10/2002 | Kawamura et al. |
| 6,574,022 | B2 | 6/2003 | Chow et al. |
| 6,661,297 | B2 | 12/2003 | Pepper |
| 6,975,397 | B2 * | 12/2005 | Hug ............................ 356/364 |

(Continued)

FOREIGN PATENT DOCUMENTS

EP 0 438 465 7/1991

(Continued)

OTHER PUBLICATIONS

Mark A. Kramer, Robert W. Boyd, Lloyd W. Hillman, and C. R. Stroud, Jr., XP-002351747 "Propagation of Modulated Optical Fields Through Saturable-absorbing Media: A General Theory of Modulation Spectroscopy," Journal of the Optical Society of America B., vol. 2, No. 9, Sep. 1, 1985, pp. 1444-1454.

(Continued)

*Primary Examiner*—Tu T Nguyen
(74) *Attorney, Agent, or Firm*—Finnegan, Henderson, Farabow, Garrett & Dunner, LLP

(57) ABSTRACT

A differential method has been developed which determines displacement from the midpoint of optical transmission (±45°) and utilizes the coupled nature of the two signals for common mode noise rejection to enhance the detection of chiral species. A beam of light is modulated, applied to the chiral mixture, and then split into a first beam and a related orthogonal beam by a polarizer or prism. The first beam and orthogonal beam are converted into electrical signals before a differential comparison of the signals is performed to detect a desired chiral species within the chiral mixture.

30 Claims, 13 Drawing Sheets

U.S. PATENT DOCUMENTS

| | | | |
|---|---|---|---|
| 7,002,685 B2 * | 2/2006 | Wang | 356/364 |
| 2003/0098746 A1 | 5/2003 | Aikawa et al. | |
| 2003/0179375 A1 | 9/2003 | Wang | |
| 2004/0046613 A1 | 3/2004 | Wissell | |
| 2004/0070766 A1 | 4/2004 | Szafraniec | |

FOREIGN PATENT DOCUMENTS

| | | |
|---|---|---|
| EP | 0 905 506 | 3/1999 |
| EP | 1 065 497 | 1/2001 |
| EP | 1 096 248 | 5/2001 |
| EP | 1 231 455 | 8/2002 |
| EP | 1 253 715 | 10/2002 |
| EP | 0 805 352 | 3/2003 |
| JP | 2002 190780 | 7/2005 |
| WO | WO 01/06918 | 2/2001 |
| WO | WO 02/25235 | 3/2002 |
| WO | WO 03/029790 | 4/2003 |

OTHER PUBLICATIONS

Phillip Gibbs, Mark Kimmel, Andreas Bommarius and Rick Trebino, "Magneto-optical Phase Enantiomeric Detector", Conference on Lasers and Electro-Optics (CLEO) 2002, Technical Digest, Post Conference Edition, Long Beach, CA, May 19-24, 2002, pp. 408-409—vol. 73, May 19, 2002 XP010606885.

National Semiconductor Application Note 597 "Current Feedback Amplifiers", Hans Palouda, pp. 1-10, Jun. 1989.

Fabrizio Barone, Enrico Calloni, Luciano Difiore, Aniello Grado, Leopoldo Milano and Guido Russo, "High-Performance Modular Digital Lock-in Amplifier," Rev. Sci. Instrum., vol. 66, No. 6, Jun. 1995, pp. 3697-3702.

Pierre-Alain Probst and Alain Jaquier, "Multiple-Channel Digital Lock-in Amplifier with PPM Resolution," Rev. Sci. Instrum. vol. 65 No. 3, Mar. 1994, pp. 747-750.

E. B. Alexandrov and V. S. Zapasskii, "Millisecond Sensitivity in Polarimetric Measurements," Opt. Spectrosc, vol. 41, No. 5, Nov. 1976, pp. 502-504.

V. S. Zapasskii, "Depression of Excess Light Noise in Polarimetric Measurements," Opt. Spectrosc.(USSR) 47 (4), Oct. 1979, pp. 450-451.

V. S. Zapasskii, "High-Sensitivity Polarimeter Based on the ILA-120 Argon Laser," Opt. Spectrosc. (USSR) 52(6), Jun. 1982, pp. 667-669.

Jonathan D. Spear and Richard E. Russo, 'Low Noise Position Sensitive Detector for Optical Probe Beam Deflection Measurements, Rev. Sci. Instrum., vol. 67, No. 7, Jul. 1996, pp. 2481-2484.

Edward Voigtman, "Effect of Source 1/f Noise on Optical Polarimeter Performance," Anal. Chem. vol. 64, No. 21, Nov. 1, 1992, pp. 2590-2595.

Oleg Mitrofanov, "Laser Excess Noise Reduction in Optical Phase-Shift Measurements," Applied Optics, vol. 42, No. 14, May 10, 2003, pp. 2526-2531.

José A. Ferrari, César D. Perciante, Alejandro Lagos, Ema M. Frins, "Improved Method For Faraday Current Sensor Data Processing," Optics Communications 199, Nov. 15, 2001, pp. 77-81.

D. Chauvat, J. Guena, Ph. Jacquier, M. Lintz, M. A. Bouchiat, M.D. Plimmer and C.W. Goodwin, "Magnification of a Tiny Polarisation Rotation by a Dichroic Plate in Balanced Mode Polarimetry," Optics Communications 138, Jun. 1, 1997, pp. 249-252.

José A. Ferrari, Alfredo Dubra, Alfredo Arnaud, and Daniel Perciante, "Current Sensor Using Heterodyne Detection," Applied Optics, vol. 38, No. 13, May 1, 1999, pp. 2808-2811.

José A. Ferrari, César D. Perciante, Alfredo Dubra, Alfredo Arnaud, and Ema M. Frins, "Alternating Current Sensor with Second-Harmonic Detection," Applied Optics, vol. 39, No. 25, Sep. 1, 2000, pp. 4638-4640.

M. Lintz, J. Guéna, M.-A. Bouchiat, and D. Chauvat, "Demonstration of an Optical Polarization Magnifier with Low Birefringence," Rev. Sci. Instrum. vol. 76, 043102, (2005), pp. 043102-1-043102-4.

Alfredo Arnaud, Fernando Silveira, Erna M. Frins, Alfredo Dubra, César D. Perciante, and José A. Ferrari, "Precision Synchronous Polarimeter with Linear Response for the Measurement of Small Rotation Angles," Applied Optics, vol. 39, No. 16, Jun. 1, 2000, pp. 2601-2604.

L. A. Barragán, J. I. Artigas, R. Alonso and F. Villuendas, "A Modular, Low-cost, Digital Signal Processor-Based Lock-in Card for Measuring Optical Attenuation," Rev. Sci. Instrum., vol. 72; No. 1, Jan. 2001, pp. 247-251.

Aloke Jain, Jayant Kumar, Fumin Zhou, Lian Li and Sukant Tripathy, "A Simple Experiment for Determining Verdet Constants Using Alternating Current Magnetic Fields," Am. J. Phys., vol. 67, No. 8, Aug. 1999, pp. 714-717.

K. Turvey, "Determination of Verdet Constant from Combined Ac and Dc Measurements," Rev. Sci. Instrum., vol. 64, No. 6, Jun. 1993, pp. 1561-1568.

Charles A. Goss, Douglas C. Wilson, and William E. Weiser, "Flow Injection Analysis with High-Sensitivity Optical Rotation Detection," Anal. Chem. vol. 66, No. 19, Oct. 1, 1994, pp. 3093-3101.

Hirofumi Kawazumi, Hideki Nishimura, Yukiaki Otsubo and Telichiro Ogawa, "Universal On-Line Detector For High-Performance Liquid Chromatography Via Magneto-Optical Rotation," Talanta, vol. 38, No. 9, 1991, pp. 965-969.

Glenn A. Laguna, "Source Noise Reduction in Diode Laser Spectroscopy Using the Faraday Effect," Applied Optics, vol. 23, No. 13, Jul. 1, 1984, pp. 2155-2158.

J. Koch, A. Zybin, and K. Niemax, "Narrow and Broad Band Diode Laser Absorption Spectrometry—Concepts, Limitations and Applications," Spectrochimica Acta Part B 57 (2002) pp. 1547-1561.

Vladimir Liger, Alexander Zybin, Yuril Kuritsyn, and Kay Niemax, "Diode-Laser Atomic-Absorption Spectrometry by the Double-Beam-Double-Modulation Technique," Spectrochimica Acta Part B 52 (1997) pp. 1125-1138.

Rongjun Wang, Yangqin Chen, Peipei CAI, Jingjing Lu, Zhiyi Bl, Xiaohua Yang and Longsheng MA, "Optical Heterodyne Velocity Modulation Spectroscopy Enhanced by a Magnetic Rotation Effect," Chemical Physics Letters 307 (1999) pp. 339-342.

Norman P. Barnes and Larry B. Petway, "Variation of the Verdet Constant With Temperature of Terbium Gallium Garnet," J. Opt. Soc. Am. B, vol. 9, No. 10, Oct. 1992, pp. 1912-1915.

E. J. Gillham, "A High-Precision Photoelectric Polarimeter," Journal of Scientific Instruments, vol. 34, Nov. 1957, pp. 435-439.

Z. P. Wang, Q. B. Li, R.Y. Feng, H. L. Wang, Z. J. Huang, and J. H. Shi, "Effects of the Polarizer Parameters upon the Performance of an Optical Current Sensor," Optics & Laser Technology 36, 2004, pp. 145-149.

P. G. L. Mills and M. O. J. Hawksford, "Transconductance Power Amplifier Systems for Current-Driven Loudspeakers," J. Audio Eng. Soc., vol. 37, No. 10, Oct. 1989, pp. 809-822.

P. G. L. Mills and M. O. J. Hawksford, "Distortion Reduction in Moving-Coil Loudspeaker Systems Using Current-Drive Technology," J. Audio Eng. Soc., vol. 37, No. 3, Mar. 1989, pp. 129-148.

James Karki, "Voltage Feedback Vs. Current Feedback Op Amps," Literature No. SLVA051, Nov. 1998, pp. 1-10, A-1-6.

Debbie Brandenburg, "Current vs. Voltage Feedback Amplifiers,"National Semiconductor Corporation, Jan. 1998, pp. 1-6.

Debbie Brandenburg, "Current vs. Voltage Feedback Amplifiers," 2002 National Semiconductor Corporation, OA-30, Jan. 1998, pp. 1-5.

Arne Buck, "Current-Feedback Myths Debunked," 2002 National Semiconductor Corporation OA-20, Jul. 1992, pp. 1-4.

W. L. L. Lenders, "The Orthocyclic Method of Coil Winding," Philip Technical Review, vol. 23, No. 12, Oct. 16, 1962, pp. 365-379.

Daniel A. DeAntonio, "Soft Magnetic Ferritic Stainless Steels," Advanced Materials & Processes, Oct. 2003, pp. 29-32.

Carlo Bertucci, Vincenza Andrisano, Vanni Cavrini and Ettore Castiglioni, "Reliable Assay of Extreme Enantiomeric Purity Values by a New Circular Dichroism Based HPLC Detection System," Chirality 12:84-92 (2000).

Prasad L. Polavarapu, "Optical Rotation: Recent Advances in Determining the Absolute Configuration," Chirality 14:768-781, 2002.

M. Bouchiat. D. Chauvat, J. Guéna, Ph. Jacquier, M. Lintz, and M. D. Plimmer, "High Precision Balanced Mode Polarimetry With a Pulsed Laser Beam," Optics Communications 119, Sep. 1, 1995, pp. 403-414.

Timothy W. King, Gerard L. Coté, Roger McNichols, Marcel J. Goetz, Jr., "Multispectral Polarimetric Glucose Detection Using a Single Pockets Cell," Optical Engineering, vol. 33, No. 8 Aug. 1994, pp. 2746-2753.

"The Benefits of DSP Lock-In Amplifiers," Optronic Laboratories, Inc., Application Note (A12), Revision A, Sep. 1996, pp. 1-8.

"Lock-In Amplifiers"225.02 Bentham Instruments Ltd., pp. 1-10, No Date.

Application Note #3, "About Lock-In Amplifiers", Stanford Research Systems, pp. 145-155, No Date.

Donald R. Bobbit, and Sean W. Linder, "Recent Advances in Chiral Detection For High Performance Liquid Chromatography," Trends In Analytical Chemistry, vol. 20, No. 3, 2001, pp. 111-123.

Peter Rozea, "Chiral Compound Analyses and Faraday Polarimetry" Application Note, Nov. 2001, pp. 20-23.

M. G. Finn, "Emerging Methods for the Rapid Determination of Enantiomeric Excess," Chirality 14:534-540, 2002 Wiley-Liss, Inc.

H. J. Lozykowski, T. Li and Z. I. Akir, "Digital Spectropolarimeter For The Measurement of Optical Polarization," Rev. Sci. Instrum., vol. 63, No. 9, Sep. 1992, pp. 4096-4101.

M. Bouchiat, D. Chauvat, J. Guéna, Ph. Jacquier, M. Lintz, and M. D. Plimmer, "High Precision Balanced Mode Polarimetry With a Pulsed Laser Beam," Optics Communications, 119, Sep. 1, 1995, pp. 403-414.

D. Chauvat, J. Guéna, Ph. Jacquier, M. Lintz, M.A. Bouchiat, M. D. Plimmer and C. W. Goodwin, "Magnification of a Tiny Polarisation Rotation By a Dichroic Plate in Balanced Mode Polarimetry," Optics Communications 138, Jun. 1, 1997, pp. 249-252.

Andreas Mandelis, Stefano Paoloni and Lena Nicolaides, "Novel Lock-In Waveform Technique for Signal-to-Noise Ratio and Dynamic-Range Enhancement in Highly Noised Photothermal Experiments," Analytical Sciences, vol. 17, Apr. 2001, pp. s5-s8.

Roger J. McNichols, Gerard L. Coté, Marcel J. Goetz, Jr., and Timothy W. King, "Linear Superposition of Specific Rotation for the Detection of Glucose" IEEE, 1993, pp. 1549-1550.

Brent D. Cameron and Gerard L. Coté, "Polarimetric Glucose Sensing in Aqueous Humor Utilizing Digital Closed-Loop Control," 18[tth] Annual International Conference of the IEEE Engineering in Medicine and Biology Society, Amsterdam 1996, pp. 204-205.

Aidan F. Browne, Todd R. Nelson and Robert B. Northrop, "Microdegree Polarimetric Measurement of Glucose Concentrations for Biotechnology Applications," IEEE, 1997, pp. 9-10.

Sunghoon Jang, Zhi Yang, Martin D. Fox and Dan Censor, "Double Lock-In Amplifier Faraday Rotation Glucometer," IEEE 2000, pp. 107-108.

Marcel J. Goetz, Jr., Martin D. Fox, MD. PH.D, and Robert B. Northrop, PH.D, "Microdegree Polarimetry Using A Diode Laser For Glucose Detection," IEEE, 1992, pp. 97-98.

Sunghoon Jang, and Martin D. Fox, "Double Lock-In Concept For More Glucose Detection," IEEE, 1999, pp. 122-124.

Michael La Marca, "Laser Interferometer Gravitational Wave Observatory," California Institute of Technology, Massachusetts Institute of Technology, Surf Final Report, Sep. 7, 2001, pp. 1-17.

C. Denise Caldwell, "Digital Lock-in Technique For Measurement of Polarization of Radiation," Optics Letters, vol. 1, No. 3, Sep. 1977, pp. 101-103.

Harry G. Brittain, "Applications of Chiroptical Spectroscopy for the Characterization of Pharmaceutical Compounds," Journal of Pharmaceutical and Biomedical Analysis 17, 1998, pp. 933-940.

"FM Spectroscopy with Tunable Diode Lasers" Application Note 7, New Focus, 2001, pp. 1-11.

Dr. Theodore Oakberg, "Linear Birefringence and Optical Rotation," PEM-90 Application Note, Hinds Instruments, Inc., 1993, pp. 1-6.

Roger J. McNichols, Brent D. Cameron and Gerard L. Coté, "Development of a Non-Invasive Polarimetric Glucose Sensor," IEEE, Apr. 1998, pp. 1-3.

V. McOmber, "Swept Coherent-heterodyne Techniques Provide High Resolutions," XP-001208118, Laser Focus World, vol. 38, No. 5, May 2002, pp. 173-178.

XP-001121554, Chien Chou, Yen-Chuen Haung, Ching-Mei-Feng and Ming Chang, "Amplitude Sensitive optical Heterodyne and Phase Lock-In Technique on Small Optical Rotation Angle Detection of Chiral Liquid", Jpn. J. Appl. Phys., vol. 36, Jan. 1997, pp. 356-359.

E. A. Avrutin, J. H. Marsh and E. L. Portnoi, "Monolithic and Multi-GigaHertz Mode-Locked Semiconductor Lasers: Constructions, Experiments, Models and Applications", IEE-Proc.-Optoelectron., vol. 147, No. 4, Aug. 2000, pp. 251-278.

Co-pending Application No. 11/120,723, Title: A Double Reference Lock-In Detector Inventor: Phillip R. Gibbs U.S. Filing Date: May 3, 2005.

Co-pending Application No. 11/168,295, Title: Systems and Methods for Chiroptical Heterodyning Inventors: Phillip R. Gibbs et al. U.S. Filing Date: Jun. 29, 2005.

Co-pending Application No. 11/168,296, Title: Systems and Methods for Automated Resonant Circuit Tuning. Inventor: Phillip R. Gibbs. U.S. Filing Date: Jun. 29, 2005.

* cited by examiner

US 7,502,111 B2

DIFFERENTIAL OPTICAL TECHNIQUE FOR CHIRAL ANALYSIS

STATEMENT REGARDING FEDERALLY SPONSORED RESEARCH

The U.S. government has certain rights to this invention by virtue of Grant #0320299 from the National Science Foundation Grant to Phillip R. Gibbs.

RELATED APPLICATIONS

This application hereby claims benefit to and incorporates by reference in their entirety earlier filed U.S. Provisional Patent Application Ser. No. 60/510,209, which was filed on Oct. 10, 2003 and U.S. Provisional Patent Application Ser. No. 60/563,364, which was filed on Apr. 19, 2004.

FIELD OF THE INVENTION

The present invention relates to chiral detectors, more particularly to a differential optical rotary dispersion detector for non-contact, rapid, and accurate screening of chiral samples.

BACKGROUND OF THE INVENTION

Optical isomers, more commonly called enantiomers, are important in several fields, including the pharmaceutical, chemical, essential oils, flavor, and food industries. The vast majority of useful drugs contain one or several chiral centers. Obtaining high enantiomeric purity of therapeutics is essential, since it is well known that the wrong enantiomer can cause harmful side effects. Thus, both producing enantiomerically pure formulations and testing for enantiomeric purity are critical. Unfortunately, both of these activities remain significant challenges, even with the current state-of-the-art analytical instrumentation. To date no generally applicable method for high throughput enantiomeric purity screening is available to the researcher.

There are known improvements to chiral analysis techniques, more specifically, in the area of reducing noise associated with the measurement of the additional optical rotation induced by a chiral sample. Single beam methods utilizing electronic or optical means to filter noise are quite common (see, for example, WO 01/06918). Other known methods utilize dual beams either by comparison to a reference cell (U.S. Pat. No. 4,912,059), mixing out of phase sinusoidal signals (U.S. Pat. No. 5,477,327), switching between a signal and reference beam (U.S. Pat. No. 5,621,528), or using a two frequency laser source with two orthogonal linear polarized waves (U.S. Pat. Nos. 5,896,198 and 6,327,037). These methods attempt to determine the displacement from the null point of optical transmission.

It is also known to use pockels cell modulation for differential chiral analysis in flow cells (U.S. Pat. No. 5,168,326). This technology involves the application of oscillating voltage to the pockels cell to produce alternating beams of linearly polarized light and circular light. By subtracting the rotation angles calculated for both beams, common sources of noise are effectively canceled out, giving a more sensitive measurement.

Thus, there remains a need to more accurately determine the additional optical rotation introduced by a chiral sample by reducing noise associated with the measurement.

SUMMARY OF THE INVENTION

A differential method has been developed which determines displacement from the midpoint of optical transmission (e.g., ±45°) and utilizes the coupled nature of the two signals for common mode noise rejection. The method and device may use lock-in detection with square wave modulation to reduce noise and improve sensitivity, may use new modulation techniques to achieve frequency modulation, may extend the technique to a multi-wavelength scanning mode, and may use a differential signal extraction mode to vastly improve sensitivity to optical rotation.

Additional aspects of the invention will be set forth in part in the description which follows, and in part will be obvious from the description, or may be learned by practice of the invention. Aspects of the invention will be realized and attained by means of the elements and combinations particularly pointed out in the appended claims. Therefore, it is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

DESCRIPTION OF THE EMBODIMENTS

Figure 1:
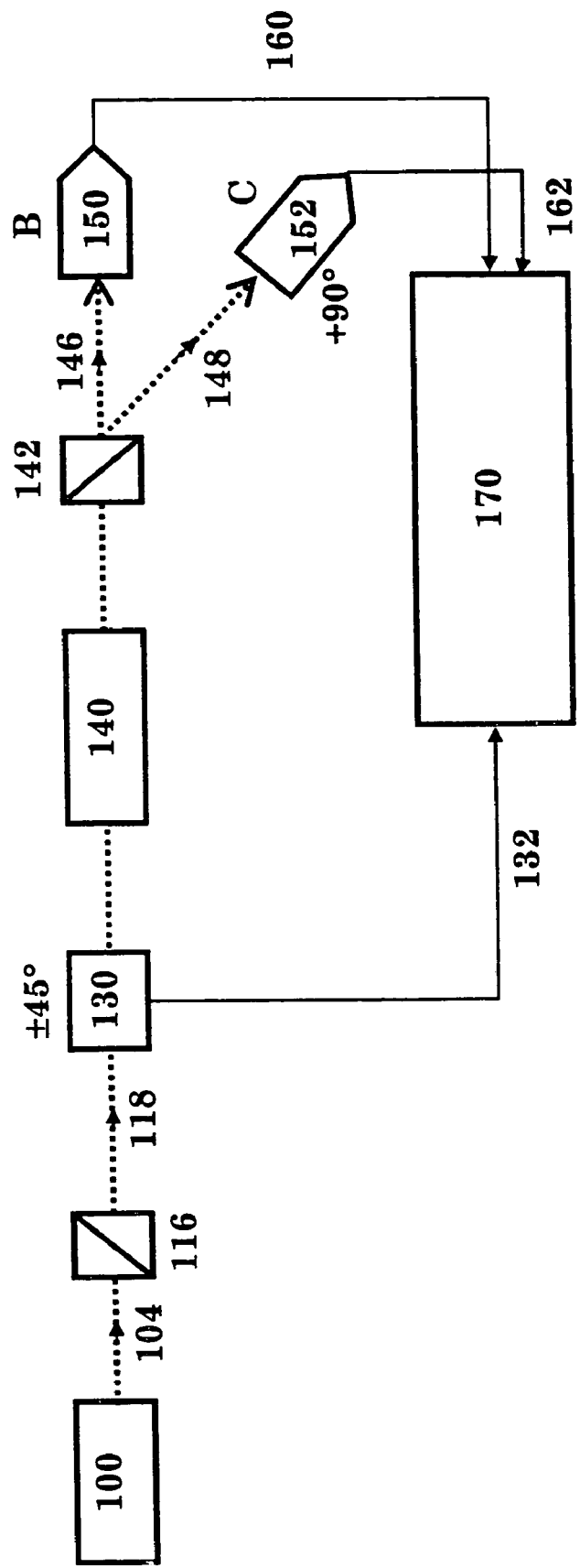
FIG. 1 is a block diagram of an embodiment of the chiral detection apparatus in accordance with principles of the present invention.

A block diagram of an embodiment of a basic differential optical rotary dispersion (DORD) apparatus in accordance with principles of the present invention is shown in FIG. 1. The basic apparatus includes light source 100, polarizer 116, signal modulator 130, sample cell 140, analyzer 142, a balanced photoreceiver (detectors B 150 and C 152) and a lock in detector 170. The light source 100 can consist of a monochromatic source such as a laser, but a wider range of wavelengths provides more useful information. In a preferred embodiment, stabilized UV and tungsten lamps may be utilized to provide a bright broad wavelength source covering the approximate range 200 to 1100 nm when implementing the light source 100 with a Hamamatsu Model L7893 series lamp. A pulsed light source may be used to avoid ambiguities associated with intermediate polarizer positions. However, in practice a continuous light source can be used and the switching time of the signal modulator may be fast enough to effectively eliminate consideration of these intermediate states.

The inlet light beam 104 passes through a polarizer 116 to produce polarized light beam 118. It is understood that any commercially available polarizer, constructed from either naturally occurring or synthetic crystals, may be used as the polarizer component. In a preferred embodiment, the polarizer includes a synthetic prism which displays superior optical properties such as a higher-extinction ratio ($>10^{-6}$) and higher damage threshold ($>500$ MW/cm$^2$ at 1064 nm) as compared to the traditional calcite. In contrast to calcite, synthetic crystals eliminate the variability in the instrumentation due to optical quality and availability. In the most preferred embodiment, the DORD polarizer 116 is implemented by a Rochon prism based on α-BBO, which has only recently become commercially available. Using an α-BBO Rochon prism allows for a wider wavelength range (190 nm to 3500 nm), yields two polarized beams, and provides a straight line path for one beam component allowing simple straight line optical configuration. Other examples of polarizers include, but are not limited to, polarization beamsplitters, GlanLaser polarizing prisms, Glan-Taylor polarizing prisms, Glan-Thompson polarizing prisms, or Wollaston prisms. Traditional polarimeters typically use Glan-Taylor polarizers which have a useful wavelength range of 350 nm to 3500 nm for calcite and narrowed ranges for α-BBO (200 to 270, 400 to 700, and 700 to 3000).

Modulation of the signal over a 90° total rotation angle, preferably ±45° from the null point, is accomplished using a signal modulator 130. However, those skilled in the art will appreciate that the principles of the present invention are not limited to modulating at a 90° total rotation angle ±45° from the null point. Indeed, there are advantages to modulation around addition points of interest that use the coupled nature of the linear polarization state as observed differentially.

The modulator converts linearly polarized light into circularly polarized light by phase-shifting one polarized light component at an angle of +45°, while phase-shifting another component at an angle orthogonal to the other (e.g., −45°). Observing at or near the midpoint of optical transmission (e.g., ±45° from the null point) is advantageous for maximum signal when the common mode noise can be efficiently rejected. This follows from derivations of Malus' Law where the intensity of transmitted light between two polarizers is described by $$I = I_o \cos^2 \theta$$

where I is the transmitted intensity, $I_o$ is the transmitted light for uncrossed polarizers and θ is the relative angle of the two polarizers with 0 degrees defined as the point of maximum transmitted light intensity.

For maximum sensitivity to chiral compounds, one should observe in a region where the change in light intensity, dI, is maximized for small changes in θ, dθ, which occurs when chiral samples are present between the two polarizers (e.g., chiral species adds or subtracts to observed total θ). Taking the derivative of Malus' equation $$dI/d\theta = 0.5 \cos 2\theta$$

and solving for dI/dθ=0, one can show that the best points for observing intensity changes due to chiral species is at ±45° from the null points of optical transmission.

The form of Malus' Law including the offset from the extinction coefficient of the polarizers, $$I = I_0 \cos^2 \theta + a$$

stated as $I = I_0 \sin^2 \theta + a$ when θ is defined relative to the null point does not change this analysis. Traditional methods do not attempt to observe chiral signals in this region due to the large light flux (½ $I_0$) common mode noise unrelated to the chiral sample.

Signal modulation can be achieved using a variety of modulation imparting devices, such as a conventional Faraday modulator or a pockels cell. In a preferred embodiment, the signal modulator is a pockels cell utilizing BBO. In addition to the same optical clarity and UV transmission characteristics of the α-BBO polarizing optics, use of a pockels cell allows square wave modulations at very high frequencies (>10 GHz) in contrast to Faraday modulators used in traditional polarimeters (~1 kHz) or photo-elastic modulators utilized in CD detectors (~50 kHz). Higher modulation frequencies are advantageous for rapid signal application using lock-in detection, synchronous detection, or balanced photodetector techniques and the use of square wave modulation has additional advantages improving signal to noise and more rapid signal acquisition as compared to sine wave modulation typically used polarimetry and CD detectors. An additional benefit is that use of a pockels cell for light modulation as compared to Faraday modulators is immunity to influence from magnetic fields. Sensitivity of traditional polarimeters can theoretically obtain $10^{-6}$ degrees of resolution but at this sensitivity the instrument acts like a compass and so is influenced by orientation in the Earths magnetic field. Thus, in commercial instruments the setup is effectively "detuned" to avoid this effect. Use of a pockels cell avoids this source of noise as the modulation is based on modulated electric fields as opposed to magnetic fields in the case of Faraday modulators.

After the beam passes through sample cell 140, it continues on to the analyzer 142 which yields two polarized beams 146 and 148, which are orthogonal to each other and diverge as they exit the analyzer. The analyzer 142 is understood to be any device capable of producing two orthogonal, diverging polarized beams. Examples of such devices include, but are not limited to, polarizing beam splitters, Wollaston prisms, or Rochon prism.

In one embodiment, it is contemplated to implement the analyzer with a Rochon prism based on α-BBO. In another embodiment, the analyzer is implemented with a Wollaston polarizer or prism, which yields two inversely coupled signal beams orthogonal to each other. The Wollaston polarizer consists of two orthogonal calcite prisms, cemented together to form a polarizing prism. Instead of focusing the light or concentrating light as it leaves the prism, the prism's configuration causes the entering light beam to diverge into two emerging beams, moving in different directions. The divergence and direction of the two exiting beams can be controlled by adjusting the placement of the prism. Accordingly, the analyzer 142 does not direct either of the light beams 146 or 148 to any target by concentrating the light. Rather, the analyzer simply deviates the light in different directions, as it does not have a focal length and cannot focus the light or concentrate the light upon any point.

Light detectors 150 and 152, at positions B and C, are utilized to transform the light signal from components 146 and 148 into voltage or current signals 160 and 162 that can be analyzed with modern electronics. In a preferred embodiment, the light detectors are photodiodes. An arrangement of the photodiodes in a balanced photodetector scheme is preferred. Observing these two beams in such a balanced photodetector scheme yields a square law detector with a high common-mode rejection ratio (CMRR). Details on the use of a balanced photodetector scheme is further discussed with regard to FIGS. 13-15.

The light detectors 150 and 152 may also be implemented with avalanche photodiodes, which amplify the detected signal internally providing extra sensitivity. In another embodiment, the light detectors are implemented with photomultiplier tubes, which have extreme sensitivity, large linear range, wide wavelength response, and low noise.

Lock-in detector 170 extracts the signal amongst the various noise signals typically present. Lock-in detection, also known as lock-in amplification and phase-sensitive detection, is a technique for reducing noise and improving sensitivity. The technique takes advantage of the fact that noise exists at all frequencies and most detectors detect all frequencies and hence see all the noise. But detecting over only a small range of frequencies can reduce noise dramatically. Lock-in detection involves periodically modulating (e.g., using a square wave, sine wave, periodic pulse, etc.) some aspect of the apparatus, leading to a sinusoidal modulation to the signal. The lock-in detector then multiplies the signal by a sine wave of the same frequency (its "reference wave"), and then it integrates over a short time (but over many periods of the sine wave). If a particular signal occurs at the correct frequency, and if it is in phase with the lock-in sine wave, then it yields a large result. On the other hand, any signal (or noise) at the wrong frequency (or the wrong phase) integrates to zero because the product of this signal and the lock-in sine wave is as often positive as it is negative. Thus, only noise of the correct frequency (and phase) contributes—in other words, much less noise. Using lock-in detection, much weaker signal levels can be detected. Typically, lock-in detection yields noise reductions of $10^6$ and hence yields similar improvements in sensitivity. Additionally, those skilled in the art will appreciate that use of a reduced modulation width allows for more wavelength discrimination.

Lock-in detection based on a square wave signals is a special case that has the advantage of increasing signal response and relaxing filtering requirements, since higher harmonics are not present, resulting in a faster response. Use of lock-in detection in conjunction with differential analysis leads to immunity from noise present in the input beam since this "common mode" noise is present in both input signals 160 and 162 and is effectively rejected by subtracting the two channel inputs to the lock-in detector. Furthermore, embodiments of the present invention have the ability to reject linear dichroism (also referred to as pseudo-rotation) from natural optical activity. The differential mode of the apparatus advantageously rejects such pseudo-rotation as common mode noise.

While not shown in the embodiment of FIG. 1, those skilled in the art will appreciate that an optional filtering scheme (not shown) may be used in any of the embodiments between the optical detectors (e.g., B150 and C 152) and the lock-in detector (e.g., detector 170) to provide further processing of the detected electrical signals (e.g., input signals 160 and 162). Basically, a filter may be used to further reduce the noise on the electrical signals prior to digital processing. While the type and specification of filter used in this embodiment may vary according to the system implementation, a preferred filter is a single active high pass analog filter used to remove undesired lower frequency signals and provide appreciable gain (with gain from an amplifier (not shown)) or at least minimal attenuation to frequencies above a preselected frequency.

The filter may also be implemented as separate filter chains providing different frequency characteristic signal outputs from each chain. The high pass filter can be fed to separate filter chains, each of which are optimized to provide gain to a desired frequency for that chain, while minimizing the gain of the undesirable frequencies. A programmable gain amplifier may also be used in each chain to provide the selective gain level. Thus, the system is able to selectively amplify signals that vary as the chiral concentration and chiral ratios vary while also being able to attenuate the others. In this manner, the filter (including individual filters and amplifiers in each chain) addresses noise issues before the input signals are digitized by analog-to-digital converters (ADC) in the lock-in detector. Those skilled in the art will appreciate that digital filtering may be used instead of or in addition to such analog filtering to further enhance noise rejection and sensitivity of the apparatus.

Figure 2:
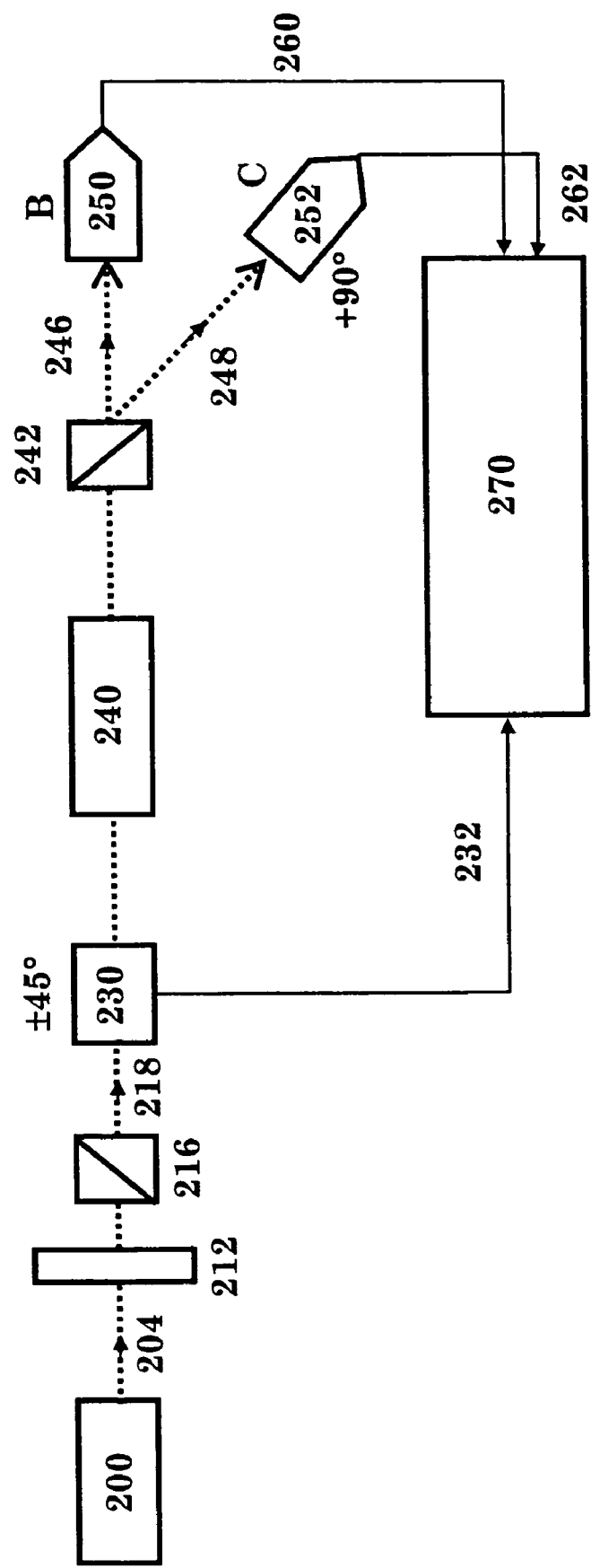
FIG. 2 is a block diagram of an embodiment of the chiral detection apparatus which optionally includes a filter in accordance with principles of the present invention.

FIG. 2 is a block diagram which illustrates an embodiment having the optional addition of a filter 212 between the light source 200 and the polarizer 216. The filter can be any commercially available filter, including but not limited to dichroic filters, interference filters, short pass, or long pass filters. In one embodiment, the filter is an acousto-optical tunable filter (AOTF). Utilizing an acousto-optical tunable filter in conjunction with stabilized UV and tungsten light sources has already been shown to allow rapid wavelength scanning, beam stabilization, and pulse shaping of the light intensity without introducing moving parts into the instrumental setup. Optimally, the filter component would provide a scanning range 200 nm to 1100 nm with less than 1 nm resolution.

Figure 3:
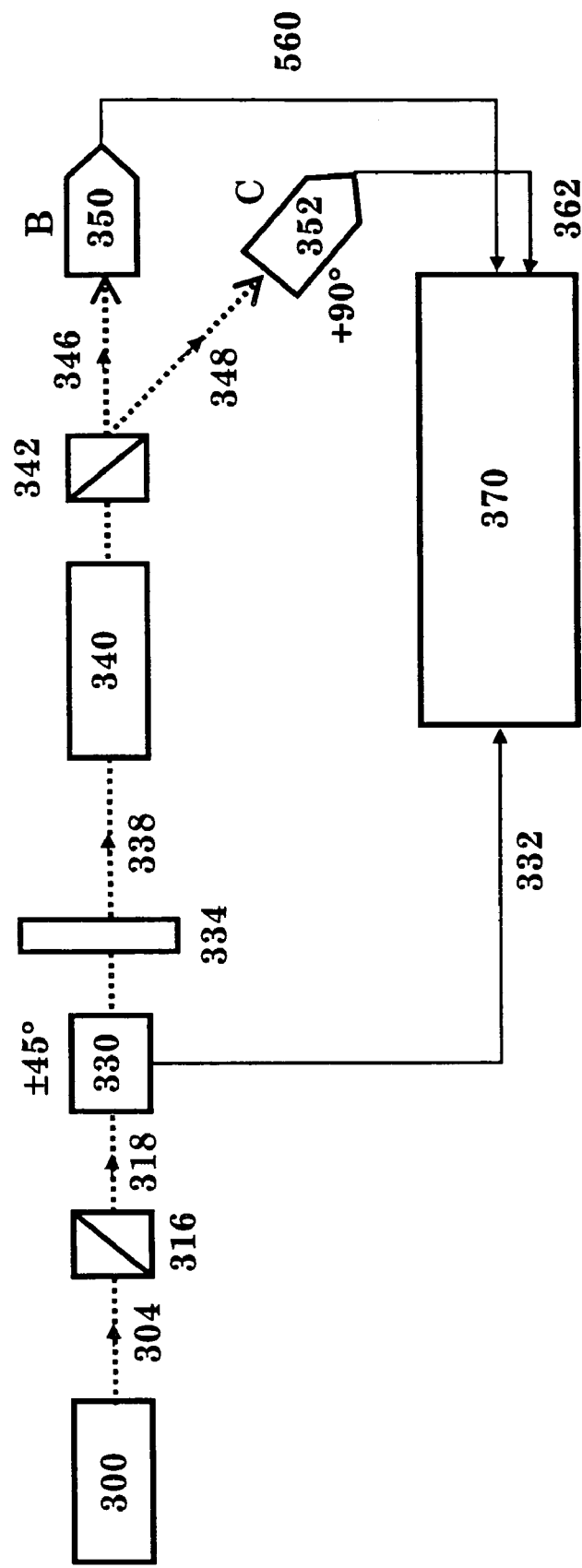
FIG. 3 is a block diagram of an embodiment of the chiral detection apparatus which optionally includes a quarter waveplate in accordance with principles of the present invention.

FIG. 3 illustrates an embodiment having the optional addition of a quarter waveplate 334 between the modulator 330 and the sample cell 340. The quarter waveplate is inserted to convert circularly polarized light from the ±45° modulation of the linear light back to linearly polarized light 338. Those skilled in the art will appreciate that quarter wave plates may be constructed from quartz, mica, or organic polymer plastics. A Fresnel rhomb may also be utilized as an achromatic waveplate.

Figure 4:
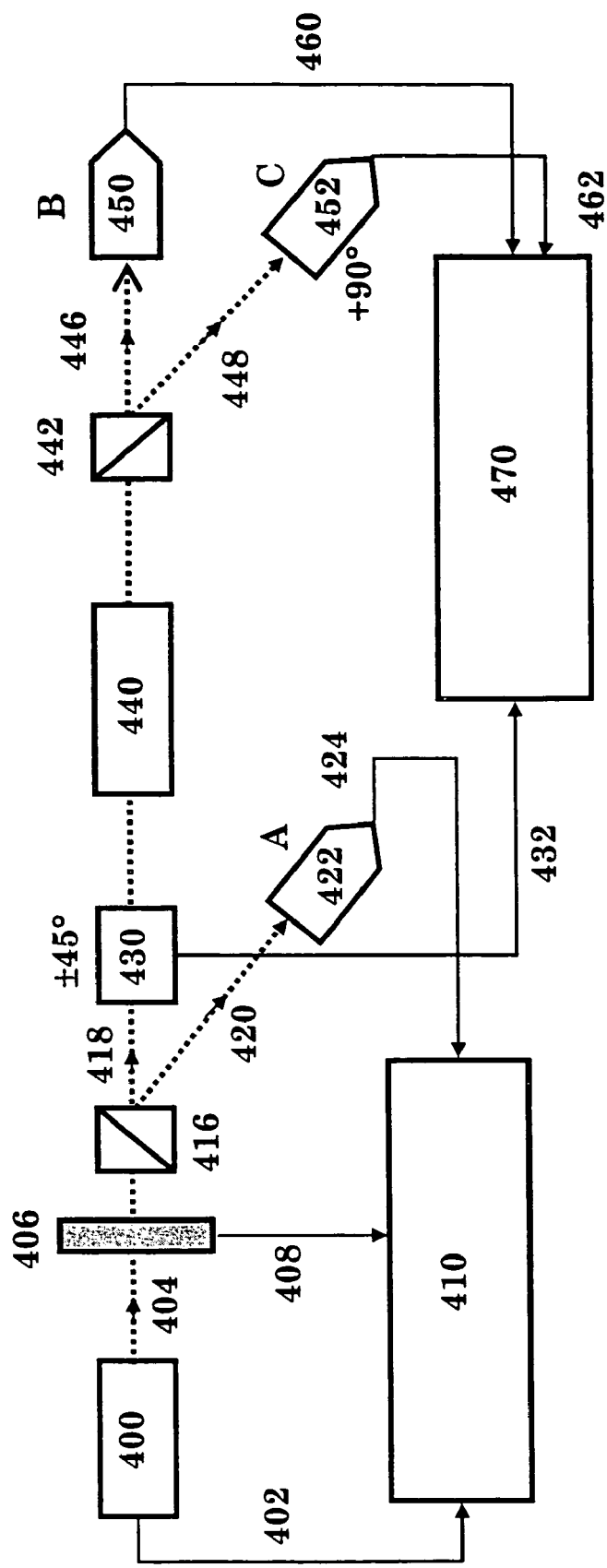
FIG. 4 is a block diagram of an embodiment of the chiral detection apparatus which optionally includes a source stabilization feedback loop in accordance with principles of the present invention.

FIG. 4 is a block diagram illustrating an embodiment having the optional addition of a source stabilization feedback loop comprising a wavelength modulator 406, an additional lock-in detector 410, and a light detector 422 at position A, which converts light intensity to a voltage or current signal 424. Polarizer 416 produces two polarized beams 418, which passes through the sample, and 420, which continues on to light detector 422. The position seen by light detector 422, is directly proportional to the input beam and if an unpolarized light source is utilized the beam intensity at light detector 422 will be equal to the transmitted beam. This is useful because noise in the beam can be suppressed with lock-in detection and a feed back loop to the wavelength modulator. The reference signal can originate from direct modulation of the light source 402 (e.g., LED or laser amplitude, pulse modulation) or a signal imposed on the transmitted light by the wavelength modulator 408.

Figure 5:
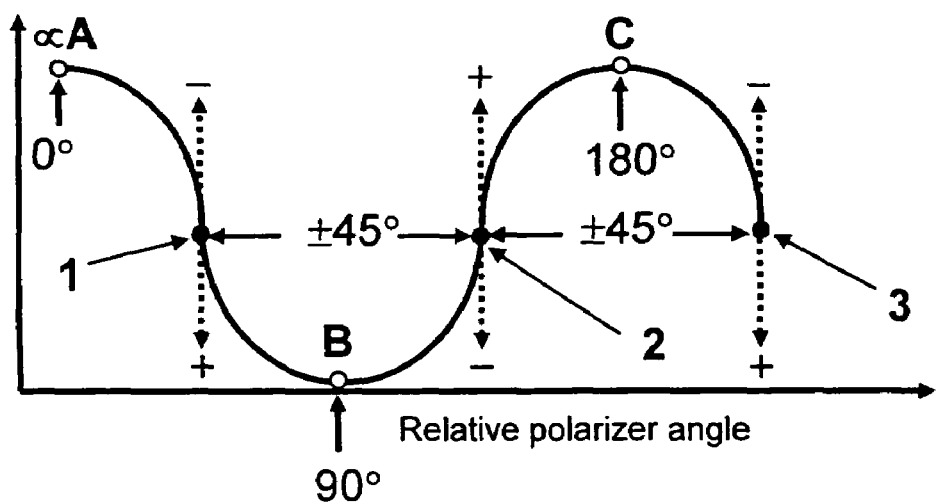
FIG. 5 is an exemplary illustration of the light transmission between two linear polarizing elements with the marked angles corresponding to the relative angle between the two polarizers, showing the relative light intensities observed by the detectors at positions B and C and the angle position resulting from signal modulation in accordance with an embodiment of the present invention.

FIG. 5 illustrates the physics describing the light intensities as observed by light detectors at positions A (FIG. 4 only), B and C (FIGS. 1-4). In general, light intensity is maximum at 0° degrees relative polarizer angle and minimum at 90°, which is commonly referred to as the "null point." The ratio of minimum transmitted light intensity at 90° and maximal transmitted intensity at 0° for an unpolarized light source is referred to as the extinction ratio. Ratios in excess of $10^{-6}$ are commercially available for the α-BBO Rochon polarizers. Higher extinction ratios effectively result in more sensitivity by minimizing polarizer leakage which was previously noted as a source of noise.

When the polarizers are properly aligned such that transmitted straight line beam intensity is minimized with no applied voltage to the pockels cell, a light detector at position B observes at 90° to the input polarizer and a light detector at position C observes at +90° from the "null point," or 180° relative to the input polarizer. When the appropriate voltage is applied to the pockels cell, the relative angle observed by light detectors at positions B and C shifts to position 1 or 2 and 2 or 3, respectively. Since the relative angle between B and C is fixed at +90° by the properties of the Rochon polarizer, the modulated observed relative angles, positions 1, 2, and 3, are coupled. Therefore when a +45° degree rotation in the beam is introduced by the pockels cell, the detector at position B observes at position 2 and the detector at position C observes at position 3. Conversely, when the opposite −45° degree rotation is introduced, the detector at position B observes at position 1 and the detector at position C observes at position 2. The critical observation is a chiral sample contributes to the beam rotation in a differential manner between 1&2 and 2&3 as shown in FIG. 5. In addition, by subtracting the intensities resulting from observation at 1&2 or 2&3 the large background signal present in each channel can be effectively rejected. This also allows one to observe the influence of chiral molecules on the beam angle in a region where the change in transmitted light intensity per degree rotation is maximal (i.e from Malus' law, $dI/d\theta=0.5 \cos 2\theta=0$ derived previously) and essentially linear for small rotations.

Figure 6:
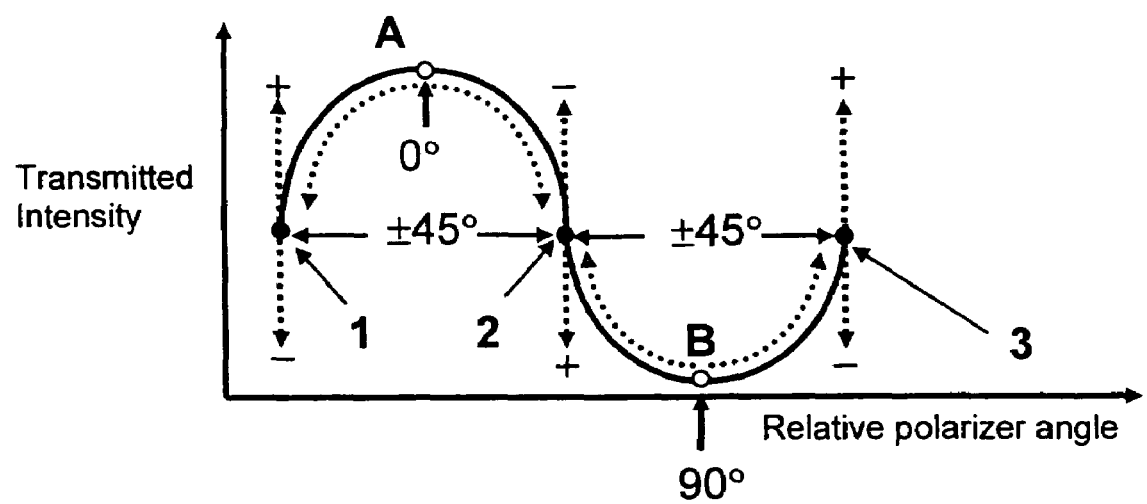
FIG. 6 is an exemplary illustration of differential detection by modulation around uncrossed (0°) and crossed (90°) polarizers in accordance with an embodiment of the present invention.
Figure 16:
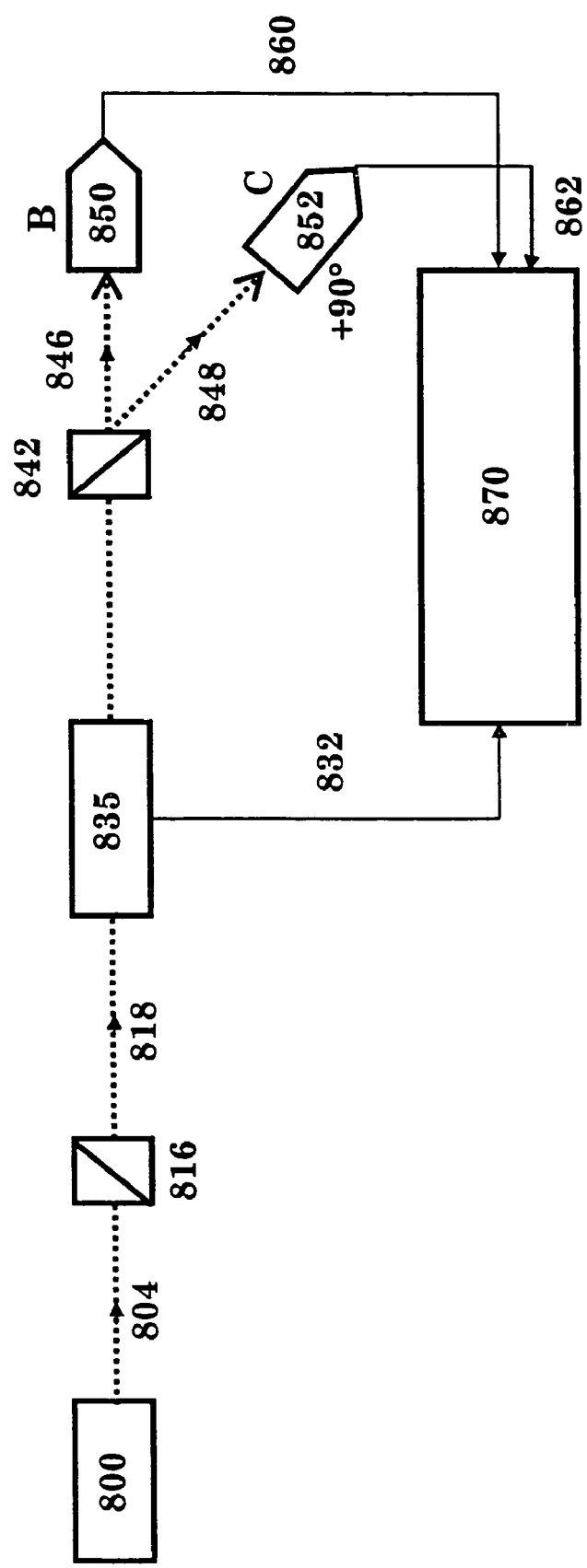
FIG. 16 is a block diagram of an embodiment illustrating a chiral detector wherein the sample is optionally modulated by a magnetic or electric field.

FIG. 6 illustrates an additional mode of differential detection, involving modulation around the 0° and 90° polarization angles. This mode of differential detection is advantageous when measurements involving Faraday Modulation are made, such as in the setup illustrated in FIG. 16. For these measurements, modulation around 0° and 90° cancels the contribution from the fundamental frequency in the Faraday modulator and any harmonica distortions present in this driving current. This is advantageous for measurements of Verdet effects, as depicted in FIG. 16, where the fundamental signals are uninteresting and would limit analog-to-digital conversion accuracy on higher harmonic or inter-modulated signal frequencies of interest. If an input Faraday modulator is used on the input probe beam to the modulated sample chamber shown in FIG. 16, observation at 0° and 90° also cancels the fundamental frequencies and harmonic distortion on this input polarization modulation in addition to those in the sample. Also, the presence of a strong beam, modulated around 0°, and a weak beam, modulated around 90°, presents an ideal case for an auto-balanced photoreceiver. The auto-balanced photoreceiver requires a strong reference beam and effectively cancels common mode noise present in both the reference and signal (weak beam at 90°). The requirement for the reference beam to be greater than or equal to the signal beam is always maintained as long as the modulation does not exceed ±45° from the 0° and 90° starting angles. Since the reference beam also contains inversely correlated signal present in the signal beam (for changes in linear polarization state of the input beam to the Wollaston polarizer), the noise rejection of the auto-balanced photoreceiver is improved and approach the shot-noise floor.

While the discussion of modulation in FIGS. 5 & 6 has been in the context of a pockels cell and a Faraday modulator, those skilled in the art will quickly appreciate the applicability of such principles to apparatus using alternative modulation devices that may be excited or modulated with different format signals (e.g., other than sine waves or square waves).

Figure 7:
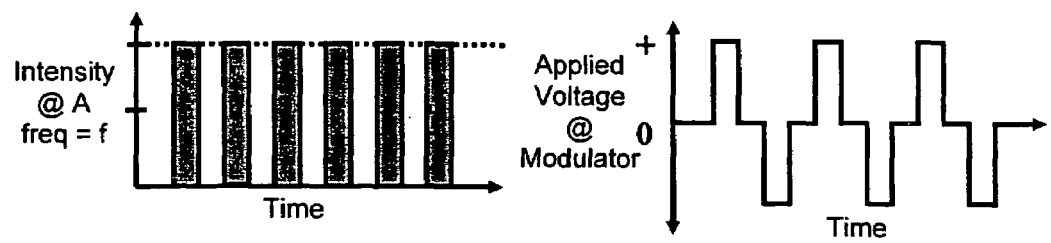
FIG. 7 is an exemplary illustration comparing the light pulses observed at position A and the signal modulation as applied to the signal modulator in accordance with an embodiment of the present invention.

FIG. 7 shows the pulsed input beam as detected at position A using lock-in detection at frequency f which is synchronized and double the frequency of the signal modulation also shown in FIG. 7. In practice, the modulation frequency used for the detector at position A can be independent of the signal modulation but for the sake of simplicity the example uses f and f/2 for the light source and signal modulation respectively.

Figure 8:
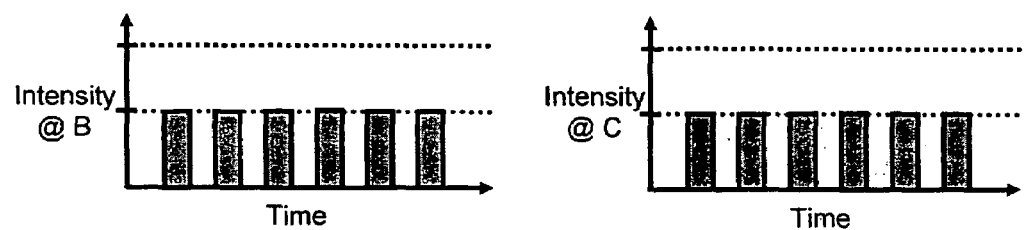
FIG. 8 illustrates exemplary resultant light intensities observed at positions B and C when no chiral sample is present in accordance with an embodiment of the present invention.
Figure 9:
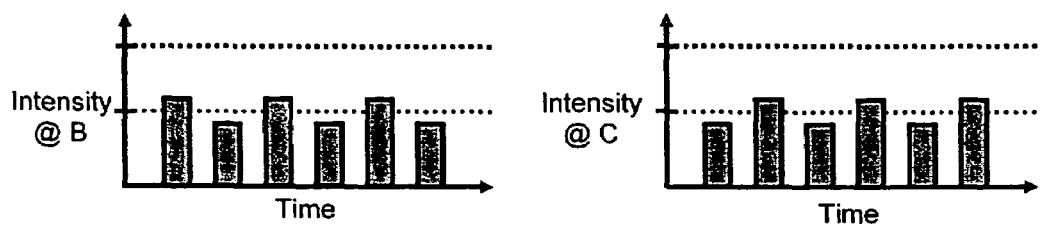
FIG. 9 illustrates exemplary resultant light intensities observed at positions B and C when a chiral sample is present in accordance with an embodiment of the present invention.
Figure 10:
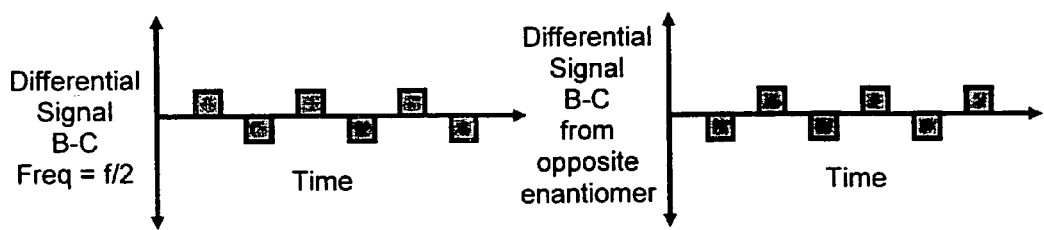
FIG. 10 is an exemplary chart showing the resulting signals for opposite enantiomers from differential comparison of the B and C channels in accordance with an embodiment of the present invention.

Once the transmitted beam passes through the sample cell the resulting intensities at positions B and C are shown in FIG. 8. At ±45° modulation these intensities are half the input beam intensity, equivalent between B and C, and thus results in zero signal when subtracted from each other. In contrast, when a chiral sample is present the two detectors observe different contributions from the samples added optical rotation as shown in FIG. 9. When the signals from B and C are subtracted for differential analysis a residual signal at the same frequency as the signal modulation, f/2 in this case, is observed as shown in FIG. 10. One should note that the signal from the opposite enantiomer produces a similar, but distinct waveform 180 degrees out of phase with the previous signal as illustrated in FIG. 10.

Figure 11:
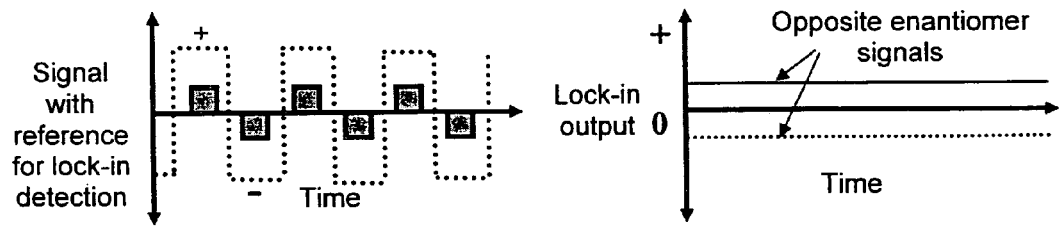
FIG. 11 is an illustration of an embodiment that demonstrates lock-in detection with square wave reference and the resulting output signal voltage for opposite enantiomers at the same concentration in accordance with principles of the present invention.

The reference square wave and signal waveform relevant to lock-in detection in one embodiment of the present invention is illustrated in FIG. 11 with the resulting DC output. The lock-in effectively sums the contribution under each half wave taking the inverse of the signal under the—half wave. For the waveform illustrated in FIG. 11, this results in a positive constant DC voltage from the amplifier. The signal waveform from the opposite enantiomer discussed previously in FIG. 10, results in a negative DC voltage of equivalent magnitude as shown in FIG. 11.

Figure 12:
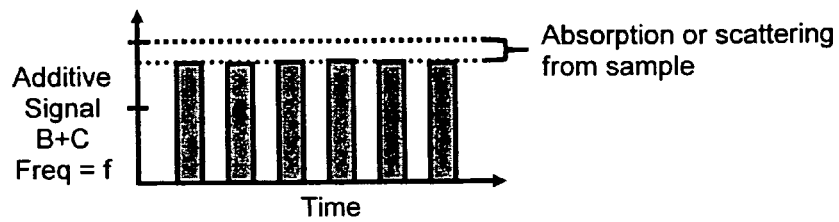
FIG. 12 shows an exemplary resulting signal from the addition of the B and C channels and the effect of absorption or scattering on the signal as compared to the input signal detected at position A in accordance with principles of the present invention.

Using the set-up described in FIG. 4, additional information can be gleaned from the dual beams by adding the signals. This is illustrated in FIG. 12. The effects of scattering or adsorption in the sample can be suppressed by normalizing the final differential signal by the detected input intensity. While this measurement is likely to contain more noise than the differential signal for the reasons discussed above (e.g., beam noise), the balanced nature of the beams and comparison to the input reference at position A should provide a normalization ratio that further suppresses noise in the final measurement due to intensity fluctuations, scattering in the sample, and simple (not CD) sample absorption. This ratio approach to normalize out these non-chiral contributions has already been demonstrated to improve traditional polarimetric measurements.

Figure 13:
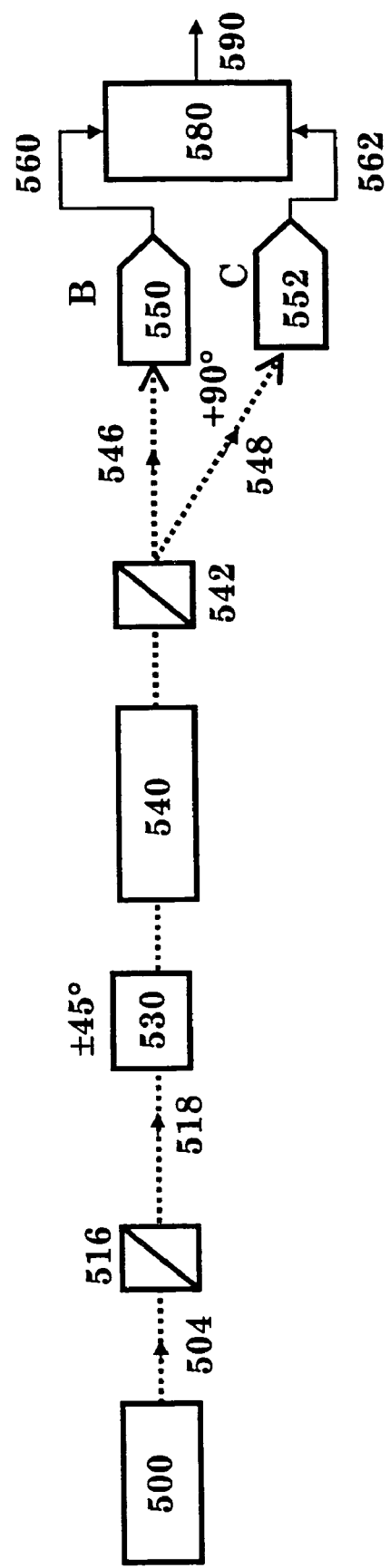
FIG. 13 is a block diagram of an embodiment illustrating differential detection using a balanced photodetection scheme in accordance with principles of the present invention.
Figure 14:
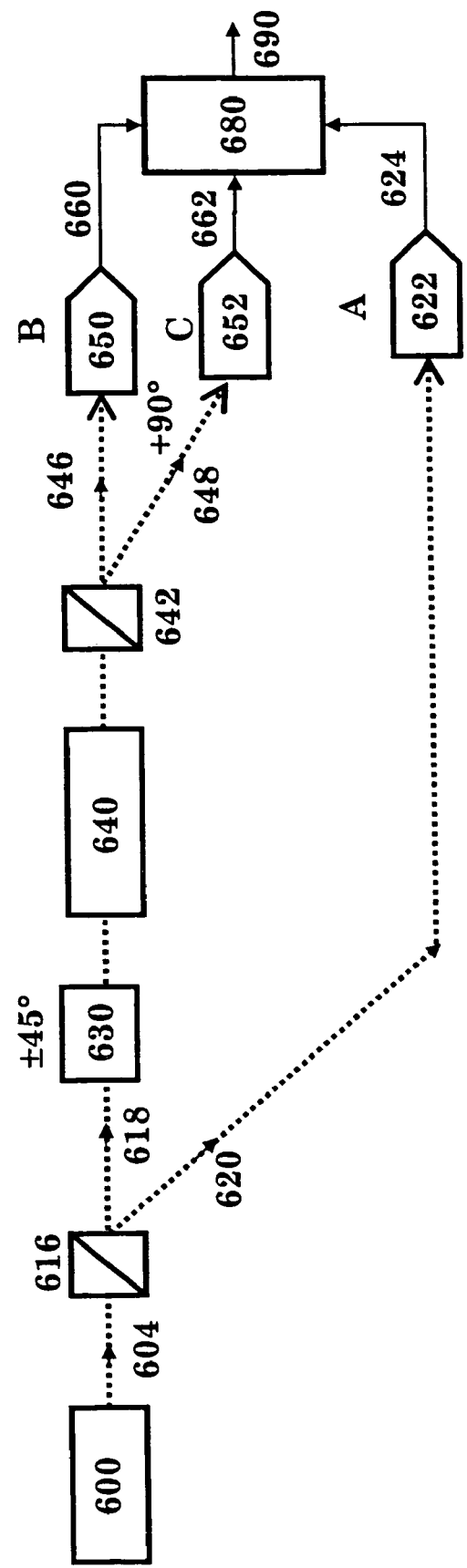
FIG. 14 is a block diagram of an embodiment illustrating differential detection using a differential and high dynamic range noise canceller in accordance with principles of the present invention.
Figure 15:
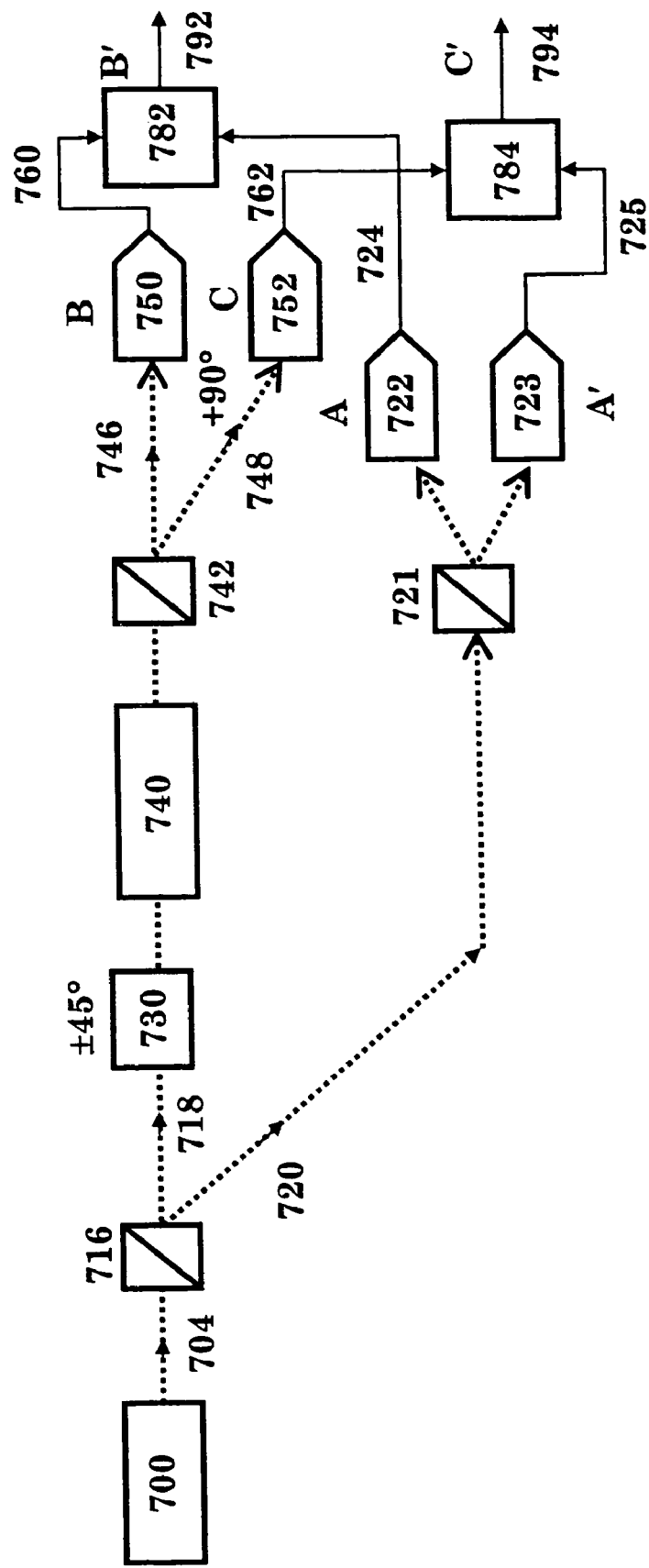
FIG. 15 is a block diagram of an embodiment illustrating differential detection using a double noise canceller scheme in accordance with principles of the present invention.

Common mode noise can also be rejected using a balanced photodector scheme as shown in FIGS. 13-15. The laser noise canceller design is a fundamentally different noise cancellation scheme as compared to lock-in detection. While lock-in detection works as a narrow bandpass filter, the noise canceller or balanced photodetector design works by subtracting photocurrents directly, with feedback applied outside the signal path to continuously adjust the subtraction for perfect balance. Thus, the excess noise and spurious modulation ideally cancel at all frequencies, leaving only the shot noise.

The noise contributions in the measurement can be described by the equation below:

$$N^2=(aI^n)^2+(bI^{n/2})^2+c^2$$

where the constants a, b, and c represent the degree of intensity fluctuations, the shot-noise limit on the intensity and the intensity-independent noise contributions, respectively.

Thus, for the case of laser intensity noise that is shot noise limited (as is typical with the balanced photodector scheme), so that a=0, and the signal is linearly dependent on laser intensity, so that n=1, then the configuration that gives the highest signal or highest resolution to small angles of rotation is at the midpoint of optical transmission ±45°.

The normalized imbalance for dual beam detection of the two orthogonally polarized beams is shown below:

$$D=(A-B)/(A+B)$$

where A and B are the two orthogonally polarized output beams and D is the normalized imbalance signal resulting from twice the inherent optical rotation of the sample ($2\alpha$). Modulating between the ±45° positions effectively doubles the measure imbalance since $D^+=-D^-$ for chiral samples. Therefore the measured imbalance $D^{meas}=D^+-D^-=2D^+=4\alpha$ or twice the signal normally observed in balanced mode polarimetry.

An additional benefit of making chiral measurements with the differential detection scheme is the insensitivity to linear birefringence, a common source of noise in polarimetry. This independence of the measured signal has been described to be from linear dichroism. The differential scheme effectively rejects signals due to linear birefringence signals (potentially refractive index noise sources as well) since the contribution is positively correlated and thus effectively rejected as common mode signal. Signal due to optical rotation is inversely correlated and thus the signal is enhanced by differential observation ($2\alpha$ or $4\alpha$ dependent on modulation scheme).

FIG. 13 is a block diagram illustrating differential detection using a balanced photodetection scheme. In this setup one of the analyzer beams 562 is used as the comparison beam into the balanced photodetector. At 45° relative to the input polarizer the two signals are of equal intensity and so signal beam 560 should be attenuated by approximately 50% for optimal balanced photodection since the comparison beam current should be roughly twice the signal beam for optimal operation. The output 590 can be detected directly or preferably sent to a lock-in detector scheme.

FIG. 14 is a block diagram of an embodiment illustrating differential detection using a differential and high dynamic range noise canceller. In this setup, the second polarized beam 620 from the polarizer 616 is used for the comparison. At 45° relative to the input polarizer the two signals are of equal intensity and so signal beam 650 should be attenuated or the relative angle should be shifted from 45° relative to input polarizer such that detector B always produces more current than detector C over the analytical range of interest (e.g., ±1°). The output can be detected directly or preferably sent to a lock-in detector scheme.

FIG. 15 is a block diagram of an embodiment illustrating differential detection using a double noise canceller scheme. In this setup, the second polarized beam 720 from the polarizer 716 is split into two comparison beams 724 and 725. At 45° relative to the input polarizer the two signals (760 and 762) are of equal intensity, but can be made to approximately 50% of the intensity of comparison beams 724 and 725 for optimal noise cancellation. The outputs, 792 and 794, can be detected directly or preferably sent to a lock-in detector scheme. A comparative analysis using (B'-C')/(B'+C') will provide the most robust signal output.

FIG. 16 illustrates an embodiment of a variation of the detector configuration shown in FIG. 1, wherein the sample 835 is modulated using a magnetic or electric field. In a typical embodiment, uniform magnetic modulation is achieved by a coil wound around the sample cell. The configuration shown in FIG. 16 will allow for differential analysis and common mode noise rejection, leading to a more sensitive technique than other known techniques.

In addition to the ability of DORD detection to accurately measure chiral rotations, the ability to rapidly scan wavelengths opens new possibilities for analyzing chiral mixtures where multiple species contribute to the optical rotation. One possibility is to use the full wavelength scan to de-convolve contributions for each species if the pure species ORD curve is known. This has been demonstrated in polarimetric measurements and is commonly utilized in adsorption studies for DNA vs. protein concentration measurements.

Figure 17:
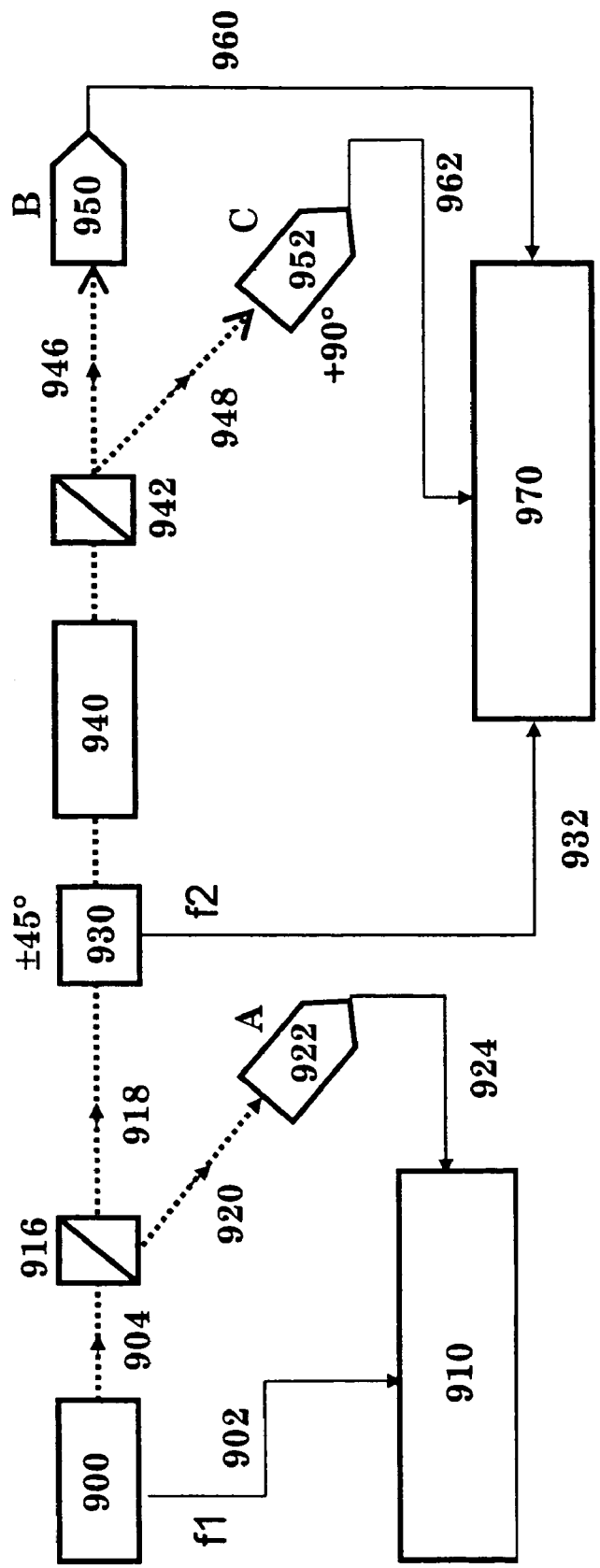
FIG. 17 is a block diagram of an embodiment illustrating circular dichroism measurements with a differential mode measurement in accordance with principles of the present invention.

FIG. 17 illustrates how a differential analysis might be applied to a circular dichroism schematic in an embodiment of the present invention. The normal absorption signal may be obtained by comparing the signal obtained by the light detector at position A at the first frequency with that obtained by adding the signals of the detectors at positions B and C at the first frequency. Furthermore, the signal detected at the second frequency, obtained by subtracting the signals obtained by the detectors at positions B and C, is due to circular dichroism and may be normalized to the detected non-chiral adsorption at the first frequency.

In addition, the ability to extend the scan into the UV allows the possibility of exploiting cotton-mouton effects (related to CD absorption maxima) in a FM-spectroscopy fashion to specifically measure individual chiral components in a mixture since the zero crossing (point where chiral rotation reverses with changing wavelength) is likely to be unique for each chiral species. This is analogous to scanning over the adsorption line in wavelength modulated or frequency modulated spectroscopy commonly known as tunable diode laser spectroscopy (TDLAS). According to published reports, there are two benefits of using modulated spectroscopy in TLDAS as compared to direct spectroscopy. First, it produces a different signal which is directly proportional to the species concentration (zero baseline technique), and second, it allows the signal to be detected at a frequency at which the laser noise is significantly reduced. Scanning over the line gives increased confidence in the measurement because the characteristic feature of the measured species is clearly seen and unwanted spectral features due to interfering species or etalon fringes can easily be identified.

Figure 18:
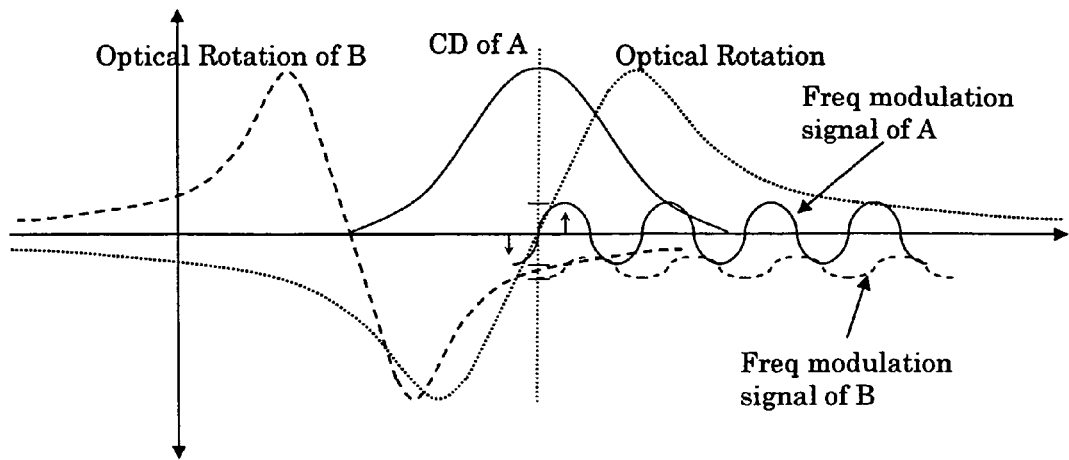
FIG. 18 shows how wavelength modulation leads to a secondary signal that is useful for discriminating species in chiral mixtures in an embodiment of the present invention.

By analogy to TDLAS, the discrimination of chiral species in a mixture can be accomplished as illustrated in FIG. 18. FIG. 18 illustrates how modulation of the probing wavelength can de-convolute the optical rotation contributions from different chiral species in an embodiment of the present invention. If the optical rotation is determined at a higher frequency modulation, a secondary modulation of the probing wavelength around the zero crossing of the optical rotation produces a modulated signal that is distinct from other chiral species with differing optical rotary dispersion curves. The first step would be to determine the optical rotary dispersion (ORD) of the components in the mixture. Ideally these would be known or alternatively the individual chiral species could be measured independently and the ORD recorded. For the example shown in FIG. 18, the mixture consists of two chiral species. The individual ORD's are shown for the species for clarity while the actual measured ORD for the mixture would be a composite of both species contributions.

In order to generate a signal specific to species A and minimize signal contributions from species B, one would preferably scan the wavelength over the zero crossing in the ORD for species A. Species A produces a much stronger modulation signal than species B when the probing wavelength is sinusoidally modulated around the zero crossing of A. This is analogous to frequency or wavelength modulated spectroscopy.

The wavelength should be scanned sinusoidally (or alternatively with other waveforms that can be detected with lock-in or other demodulation techniques) over this crossing. This converts the wavelength modulation into an amplitude modulation superimposed on the detected chiral signal. The optimum modulation width and frequency are interrelated by the speed at which the wavelength can effectively be varied and signal contributions from other species. For acousto-optical tunable filters this speed is approximately 0.5 nm per microsecond, so scanning over a 10 nm region would result in a 10 kHz signal as shown in FIG. 18. Scanning over a larger interval would increase the amplitude modulation but decrease the modulation frequency and potentially increase contributions from other species.

Pragmatically, the simplest procedure would be to pick a spectral modulation width that achieves a favorable signal to noise ratio in the available noise spectrum and then scan the solution over the available spectral range at this fixed width.

Figure 19:
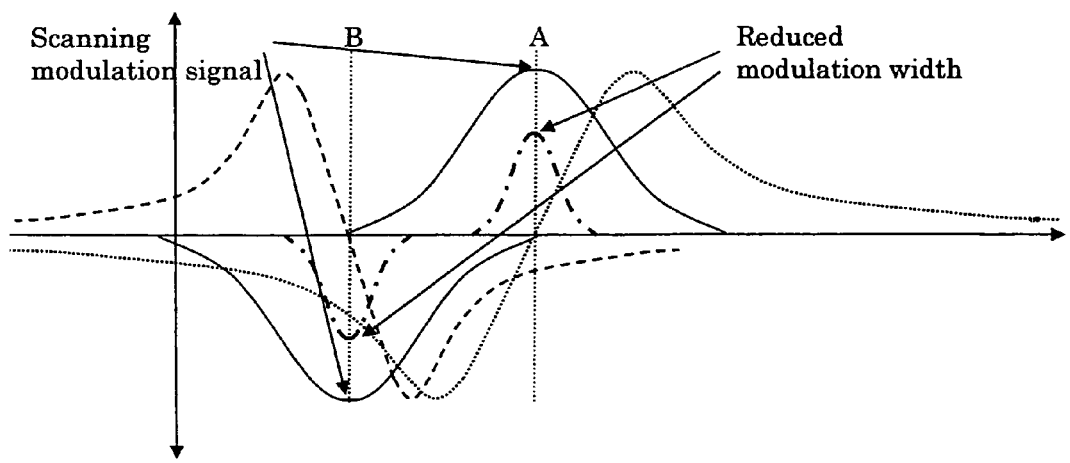
FIG. 19 shows an exemplary signal resulting from a fixed modulation width scanned over the available wavelengths in a chiral mixture with two chiral species and detected at the modulation frequency in accordance with an embodiment of the present invention.

This results in the information shown in FIG. 19 and is analogous to an adsorption CD scan but is actually a scan of the derivative of the ORD. Signals resulting from the individual species are shown as absorption peaks. Enhanced discrimination can be obtained by narrowing the modulation width, as illustrated by the second set of peaks which are smaller due to the reduced amplitude modulation, but more cleanly separated. This process presumes that the chiral signature is accurately measured at a higher frequency than the wavelength modulation frequency.

Using this technique to resolve individually species in chiral mixtures can provide real-time kinetic information for chiral enzymatic reactions. This information may be difficult to impossible to obtain using current real-time methods, such as polarimetry and circular dichroism, because they are only able to report the total property of the sample (e.g., optical rotation or circular dichroism) and not the individual species contributions to the detected signal. Circular dichroism can improve the signal-to-noise (S/N) ratio by observing at the adsorption maxima of one species of interest but other chiral species can still contribute unless their CD spectrum is far removed from the species of interest. Some obvious chiral enzymatic reactions of pharmaceutical interest are those involving alcohol dehydrogenases, racemases and isomerases.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of detecting an angle of optical rotation of a chiral sample, comprising the steps of:
    generating an input light beam from a light source;
    polarizing the input light beam to obtain a beam of linearly polarized light;
    modulating the beam of linearly polarized light such that it is at least substantially near the midpoint of optical transmission to produce a modulated beam;
    transmitting the modulated beam through a sample solution to yield a signal beam;
    splitting the signal beam into a first polarized signal beam and a second polarized signal beam, the second polarized signal beam being orthogonal to the first polarized signal beam;
    measuring the light intensity of the first polarized signal beam and the second polarized signal beam;
    converting the light intensity of the first polarized signal beam and the second polarized signal beam into a first signal voltage or current and a second signal voltage or current; and
    subtracting the second signal voltage or current from the first signal voltage or current to obtain an output signal voltage or current corresponding to twice the angle of optical rotation for the chiral sample.

2. The method according to claim 1 further comprising filtering the input light beam.

3. The method according to claim 1 further comprising filtering the first signal voltage or current and the second signal voltage or current.

4. The method according to claim 3, wherein the filtering step is accomplished with at least one from the group of a digital filter and an analog filter.

5. The method according to claim 3, wherein the filtering step further comprises selectively filtering the first signal voltage or current and the second signal voltage or current and selectively amplifying the first signal voltage or current and the second signal voltage or current.

6. The method according to claim 1 further comprising linearly polarizing the modulated beam.

7. The method according to claim 1 further comprising stabilizing the light source using a feedback loop.

8. The method according to claim 7, wherein the stabilizing step further comprises:
- modulating the input light beam to produce a modulated input beam;
- polarizing the modulated input beam to yield a first linearly polarized input beam, and a second linearly polarized input beam, the first linearly polarized input beam passing through the sample solution;
- measuring the light intensity of the second linearly polarized input beam;
- converting the light intensity of the second linearly polarized input beam into an input signal voltage or current;
- comparing the input signal voltage or current to a reference signal obtained from the input light beam or the modulated input beam.

9. A method according to claim 7 further comprising normalizing the effects of non-chiral contributions.

10. An apparatus for detecting an angle of optical rotation of a chiral sample, comprising:
- a light source for generating an input light beam;
- a polarizer for converting the input light beam into a beam of linearly polarized light;
- a modulator for modulating the beam of linearly polarized light such that it is at least substantially near the midpoint of optical transmission to produce a modulated beam;
- a sample cell for containing the chiral sample, through which the modulated beam can pass to produce a signal beam;
- an analyzer for splitting the signal beam into a first polarized signal beam and a second polarized signal beam, the second polarized signal beam being orthogonal to the first polarized signal beam;
- a first light detector for measuring the light intensity of the first polarized signal beam and converting the light intensity into a first signal voltage or current;
- a second light detector for measuring the light intensity of the second polarized signal beam and converting the light intensity into a second signal voltage or current; and
- a comparative circuit for subtracting the second signal voltage or current from the first signal voltage to obtain an output signal voltage or current corresponding to the angle of optical rotation for the chiral sample.

11. The apparatus of claim 10 further comprising a filter for filtering the input beam.

12. The apparatus according to claim 11, wherein the filter is selected from the group consisting of dichroic filters, interference filters, short pass filters, long pass filters, and acousto-optical tunable filters.

13. The apparatus according to claim 10 further comprising a first filter for filtering the first signal voltage or current and a second filter for filtering the second signal voltage or current.

14. The apparatus according to claim 13, wherein the first filter and the second filter are at least one from the group of a digital filter and an analog filter.

15. The apparatus according to claim 13, wherein the first filter selectively filters and selectively amplifies the first signal voltage or current and the second filter selectively filters and selectively amplifies the second signal voltage or current.

16. The apparatus of claim 10 further comprising a quarter waveplate for linearly polarizing the modulated beam.

17. The apparatus of claim 16, wherein the quarter waveplate is constructed from a material selected from the group consisting of quartz, mica, and organic polymer plastics.

18. The apparatus of claim 10 further comprising a source stabilization feed back loop comprising:
- a wavelength modulator for modulating the input light beam to produce a modulated input beam;
- a second polarizer for converting the modulated input beam into a first linearly polarized input beam and a second linearly polarized input beam, the first linearly polarized input beam passing through the sample solution;
- an additional light detector for measuring the light intensity of the second linearly polarized input beam and converting the light intensity into an input signal voltage or current;
- an additional comparative circuit for comparing the input signal voltage or current to a reference signal obtained from the light source or the wavelength modulator.

19. An apparatus according to claim 10, wherein the light source is pulsed or continuous.

20. An apparatus according to claim 10, wherein the light source isone from the group comprising a laser, a stabilized UV lamp, and a tungsten lamp.

21. An apparatus according to claim 20, wherein the stabilized UV lamp or tungsten lamp covering the wavelength range of 200 to 1100 nm.

22. An apparatus according to claim 10, wherein the polarizer is composed of both synthetic and naturally occurring crystal.

23. An apparatus according to claim 10, wherein the polarizer is a Glan-Taylor polarizing prism, a Glan-Thompson polarizing prism, a Wollaston prism, or a Rochon prism.

24. An apparatus according to clam 23, wherein the Rochon prism is composed of α-BBO.

25. An apparatus according to claim 10, wherein the modulator is a pockels cell or a Faraday modulator.

26. An apparatus according to claim 10, wherein the analyzer is one of a group comprising a polarizing beam splitter, a Wollaston prism, and a Rochon prism.

27. An apparatus according to claim 26, wherein the Rochon prism is composed of α-BBO.

28. An apparatus according to claim 10, wherein the first light detector and second light detector are photodiodes or photomultiplier tubes.

29. An apparatus according to claim 28, wherein the photodiodes are arranged in a balanced photodetector scheme.

30. An apparatus according to claim 10, wherein the lock-in detector is based on sinusoidal or square wave signals.

* * * * *